United States Patent [19]

Gauri

[11] Patent Number: 4,511,557

[45] Date of Patent: Apr. 16, 1985

[54] PHARMACEUTICAL COMPOSITION

[76] Inventor: Kailash K. Gauri, Zur Waldburg 13, Lentföhrden, Fed. Rep. of Germany, D 2359

[21] Appl. No.: 409,993

[22] Filed: Aug. 20, 1982

[30] Foreign Application Priority Data

Aug. 24, 1981 [DE] Fed. Rep. of Germany ....... 3133445

[51] Int. Cl.$^3$ ............................................ A61K 35/14
[52] U.S. Cl. ................................... 514/263; 514/345; 514/576
[58] Field of Search ................ 424/101, 253, 251, 263

[56] References Cited

PUBLICATIONS

Stefanovich et al.—Chem. Abst. vol. 86 (1977) p. 37640k.
Steen et al.—Chem. Abst. vol. 95 (1981) p. 509j.

*Primary Examiner*—Sam Rosen
*Attorney, Agent, or Firm*—Charles A. Muserlian

[57] ABSTRACT

Compositions for increasing oxygen supply in tissue of warm-blooded animals comprising at least one vasoactive compound selected from the group consisting of (a) calcium 2,5-dihydroxy-phenylsulfonate, (b) a 3,7-dihydro-3,7-dialkyl-1H-purine-2,6-dione of the formula wherein AlK and AlK' are individually alkyl of 1 to 4 carbon atoms, n is an integer from 2 to 4 and R is selected from the group consisting of $$-\overset{O}{\underset{\|}{C}}-HC_3$$

and $-CH_2-CH_3$, (c) a pyrazolo-[3,4-d]pyrimidine of the formula wherein $R^1$ and $R^2$ are individually selected from the group consisting of hydrogen, alkyl of 1 to 8 carbon atoms, alkenyl of 2 to 8 carbon atoms and alkylcarbonylalkyl of 4 to 8 carbon atoms with the proviso that $R^1$ and $R^2$ are not both hydrogen and A is selected from the group consisting of wherein $R^3$ is selected from the group consisting of hydrogen and alkyl of 1 to 4 carbon atoms and $R^4$ is selected from the group consisting of hydrogen, alkyl of 1 to 6 carbon atoms and alkenyl of 2 to 6 carbon atoms, (d) a pyridone of the formula wherein m is an integer from 2 to 4 and $R^5$ is selected from the group consisting of $$\overset{O}{\underset{\|}{-C-CH_3,}}$$

$-CH_2-CH_3$ and $-CH_2-CH_2-OH$ and (e) a compound selected from the group consisting of nicergoline, vincamine and dipyridamol and a potentiating amount of a dialyzed concentrate of deproteinized calf's blood with the blood constituents having a molecular weight less than 10,000 and method for increasing oxygen supply to animal tissues.

8 Claims, No Drawings

PHARMACEUTICAL COMPOSITION

The invention relates to novel pharmaceutical compositions on the basis of vasoactive compounds in combination with certain biological active ingredients which are capable of promoting oxygen supply in the tissue.

The oxygen promoting natural ingredient, preferably employed, is a dialysate concentrate obtained from deproteinized calf blood and contains complete blood constituents of the molecular weight below 10,000.

The vasoactive compounds include for example calciumdobesilate, pentoxifyllin, pentifyllin, dipyridamol, pyrazolopyrimidines and pyridinol-1-(n-hexanon-5).

It is known that the vasoactive compounds as described herein can improve the blood circulation in central and in peripherel regions, including the retinal area as well. For example their efficacy in the retina can be evaluated experimentally by means of the electroretinogramme (ERG) using the methyl- or the allylalkohol intoxication.

Further it is known that the vasoactive compounds at higher dose level, for example already at double the therapeutically effective concentration can injure the retinal function (K. K. GAURI, in: Problematik der arzneimittelbedingten Oculotoxizität. AMI Berichte 2/1980. Ed. Grosdanoff, Hockwin, Koch, Schnieders. Dietrich Reimer-Verlag, Berlin 1980; pages 33–39). Therefore the vasoactive drugs exhibit a narrow therapeutic index. Especially by long term treatment, which is the case for the vasoactive drugs, they are liable to produce toxic side effects.

Aim of the invention is to create drug for the treatment of circulatory disorders which exhibit broader therapeutic index, that is which show large range between the effective and the toxic dose levels.

Unanticipatedly it has been found now, that a combination of oxygen promoting biologically active principal as described above with a vasoactive drug can considerably increase the therapeutic index.

The vasoactive compounds employed are following:
(i) 2,5-dihydroxyphenylsulfonicacid-calcium, also known as calciumdobesilate
(ii) a 3,7-dihydro-3,7-di-$C_{1-4}$-alkyl-1-(5-substituted)-1H-purine-2,6-dion of the structure I

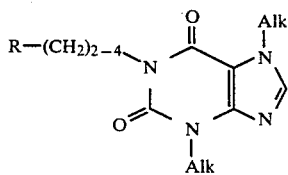

wherein Alk designate the same or different linear or branched lower alkyl residues of 1 to 4 C-atoms and R is a

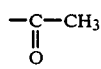

or —$C_2H_5$ group.

(iii) a pyrazolo-[3,4-d]-pyrimidine of the general formulae

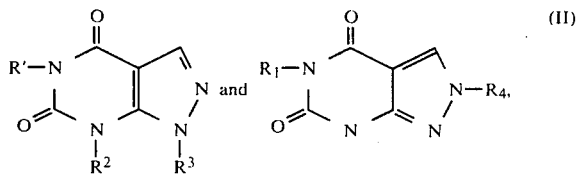

wherein $R^1$ and $R^2$ can possess the same or different significance and constitute a H-atom or $C_1$–$C_8$-alkyl radical, $C_2$–$C_8$-alkenyl, $C_4$–$C_8$-alkyl-carbonylalkyl groups, however $R^1$ and $R^2$ cannot be H-atoms at the same time, $R^3$ is a H-atom or a $C_1$–$C_4$-alkyl group and $R^4$ is a H-atom, $C_1$–$C_6$-alkyl or $C_2$–$C_6$-alkenyl group; preferably $R^1$, $R^3$ as methyl, ethyl and $R^2$ as

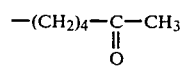

(iv) a pyridone of the formula III

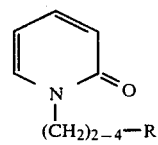

wherein R is a

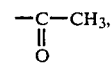

—$C_2H_5$ or —$C_2H_4OH$ residue (v) Nicergoline, Vincamine or Dipyridamol.

Preferential compounds of the formula I are the above mentioned Pentifyllin and the Pentoxifyllin. The active consituents mentioned under (i), (ii) and (v) are known, see i.e. "The Merck Index", 9.edition, Nr. 3407, 6927, 6931, 9638, 6310 and 3366.

The pyrazolopyrimidines of the general formula II are prepared in that the 4-hydrazinouracil of the formula IIa:

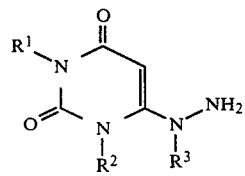

wherein $R^1$, $R^2$ and $R^3$ possess the above mentioned significance are treated with a mixture of phosphoroxychloride and dimethylformamide for example according to the method described in DE-AS No. 1 186 466. After the addition of the hydrozinouracil is complete, the mixture is allowed to reach the room temperature. Upon pouring onto the ice the desired product separates out.

Provided one of the residues $R^1$ or $R^2$ is an alkylcarbonylalkyl group, profitably one can proceed in the way, that the corresponding 4,5,6,7-tetrahydro-4,6-dioxo-pyrazolo-[3,4-d]-pyrimidine is alkylated with a ω-ω'-dibromalkane to ω-alkyl derivative which is treated with acetoaceticester and the reaction product is subjected to a ketone decomposition reaction. For example by such a reaction with the 7-ethyl-4,5,6,7-tetrahydro-1-methyl-4,6-dioxo-1H-pyrazolo-[3,4-d]-pyrimidine with 1,3-dibromopropane, the 5-(3-bromopropyl)-7-ethyl-4,5,6,7-tetrahydro-1-methyl-4,6-dioxo-1H-pyrazolo-[3,4-d]-pyrimidine is obtained, which upon acetoaceticester condensation and subsequent ketone decomposition yields the 7-ethyl-4,5,6,7-tetrahydro-1-methyl-4,6-dioxo-5-(5-oxo-n-hexyl)-1H-pyrazolo-[3,4-d]-pyrimidine. The alkylcarbonylalky rest can also be introduced by direct alkylation reaction of the appropriate 4,5,6,7-tetrahydro-4,6-dioxo-pyrazolopyrimidine, preferably as a sodium salt, with an alkylcarbonylalkyl-hologenide, preferably a chloride or a bromide. For example a 5-oxo-n-hexyl group can be introduce by using 1-bromohexanone-5.

The pyridones of the formula III are described in the German patent application P No. 22 289 and P No. 22 25 229.

Examples for the preferntial compounds of the formula II are following:

7-n-Hexyl-4,5,6,7-tetrahydro-1,5-dimethyl-4,6-dioxo-1H-pyrazolo[3,4-d]-pyrimidin (Schmp. 111° C.);

5-n-Hexyl-4,5,6,7-tetrahydro-1,7-dimethyl-4,6-dioxo-1H-pyrazolo[3,4-d]-pyrimidin;

7-i-Butyl-4,5,6,7-tetrahydro-1,5-dimethyl-4,6-dioxo-1H-pyrazolo[3,4-d]-pyrimidin;

2-Ethyl-5-n-hexyl-4,5,6,7-tetrahydro-7-methyl-4,6-dioxo-2H-pyrazolo-[3,4-d]pyrimidin (Schmp. 110° C.);

2-n-Butyl-7-n-hexyl-4,5,6,7-tetrahydro-5-methyl-4,6-dioxo-2H-pyrazolo-[3,4-d]pyrimidin (Schmp. 67° C.);

4,5,6,7-Tetrahydro-5-methyl-4,6-dioxo-7-(5-oxo-n-hexyl)-2H-pyrazolo-[3,4-d]pyrimidin;

4,5,6,7-Tetrahydro-1-methyl-4,6-dioxo-5-(5-oxo-n-hexyl)-3-n-propyl-1H-pyrazolo[3,4-d]pyrimidin;

5-n-Hexyl-4,5,6,7-tetrahydro-2,7-dimethyl-4,6-dioxo-2H-pyrazolo[3,4-d]-pyrimidin (Schmp. 73°–75° C.);

2-n-Butyl-5-n-hexyl-4,5,6,7-tetrahydro-7-methyl-4,6-dioxo-2H-pyrazolo-[3,4-d]pyrimidin (Schmp. 88°–90° C.);

2,5-Di-n-hexyl-4,5,6,7-tetrahydro-7-methyl-4,6-dioxo-2H-pyrazolo[3,4-d]-pyrimidin (Schmp. 80°–81° C.);

7-n-Hexyl-4,5,6,7-tetrahydro-5-methyl-4,6-dioxo-2H-pyrazolo[3,4-d]-pyrimidin (Schmp. 159°–161° C.)

7-n-Hexyl-4,5,6,7-tetrahydro-2,5-dimethyl-4,6-dioxo-2H-pyrazolo[3,4-d]-pyrimidin (Schmp. 109°–110° C.);

2,7-Di-n-hexyl-4,5,6,7-tetrahydro-5-methyl-4,6-dioxo-2H-pyrazolo[3,4-d]-pyrimidin (Schmp. 96°–97° C.);

4,5,6,7-Tetrahydro-2-methyl-4,6-dioxo-7-(5-oxo-n-hexyl)-2H-pyrazolo-[3,4-d]pyrimidin;

7-Allyl-2-n-hexyl-4,5,6,7-tetrahydro-1,5-dimethyl-4,6-dioxo-2H-pyrazolo-[3,4-d]pyrimidin;

4,5,6,7-Tetrahydro-3,5-dimethyl-7-(2-methylbutyl)-4,6-dioxo-1H-pyrazolo[3,4-d]pyrimidin;

4,5,6,7-Tetrahydro-1,5-dimethyl-7-(2-methylbutyl)-4,6-dioxo-1H-pyrazolo[3,4-d]pyrimidin;

7-n-Hexyl-4,5,6,7-tetrahydro-5-methyl-4,6-dioxo-2-n-propyl2H-pyrazolo-[3,4-d]pyrimidin;

4,5,6,7-Tetrahydro-1,5-dimethyl-4,6-dioxo-7-(5-oxo-n-hexyl)-1H-pyrazolo[3,4-d]pyrimidin;

2-Ethyl-7-n-hexyl-4,5,6,7-tetrahydro-5-methyl-4,6-dioxo-2H-pyrazolo[3,4-d]pyrimidin (Schmp. 96°–97° C.);

5-n-Hexyl-4,5,6,7-tetrahydro-7-methyl-4,6-dioxo-1H-pyrazolo[3,4-d]pyrimidin (Schmp. 138° C.);

3-Ethyl-5-n-hexyl-4,5,6,7-tetrahydro-1,7-dimethyl-4,6-dioxo-1H-pyrazolo[3,4-d]pyrimidin;

5-n-Hexyl-4,5,6,7-tetrahydro-3-(3,4,5-trimethoxyphenyl)-1,7-dimethyl-4,6-dioxo-1H-pyrazolo[3,4-d]pyrimidin;

7-i-Butyl-4,5,6,7-tetrahydro-5-methyl-4,6-dioxo-1H-pyrazolo[3,4-d]pyrimidin (Schmp. 204° C.);

4,5,6,7-Tetrahydro-3-(2-hydroxyethyl)-4,6-dioxo-5-(3-oxobutyl)-2H-pyrazolo[3,4-d]pyrimidin.

The other component of the invention, the dialysate concentrate of deproteinized calf blood is described in the German Pat. Nos. 1 017 744 and 1 076 888 and in the application Nos. 1 949 195, 1 617 355 and 2 325 196 wherein the blood of freshly slaughtered oxen and horses is mixed and then subjected to haemolysis by stirring wth apyrogenic distilled water in a 1 to 1 ratio of water to blood, followed by filtration and enzymatic hydrolysis with papaine at 35° to 42° C. and a pH of 5 to 5.5, heating the resulting product to 80° C. to deproteinize the same followed by immediate cooling and filtration and concentration under vacuum at low temperatures to 5% of its original volume, subjecting the water to a further deproteinization by treatment with ethanol after which the ethanol is distilled under vacuum and the product is diluted with apyrogenic distilled water and filtered and the product is then extracted with chloroform to remove lipids, followed by removal of the chloroform and passing the resulting product through an ion exchange resin after dilution with water to remove histamine and drying the resulting extract.

The composition of the invention contains one or more of the vasoactive compounds in combination with the above mentioned natural oxygen promoting product, the dialysate concentrate from deproteinized blood, preferably calf blood in a usual liquid or a solid pharmaceutical carrier.

The composition of invention can be applied parenterally, preferably as aqueous solutions with or without solvents or orally as solid or liquid formulations i.e. tablets, pills or as drops. If desired, they can also be employed as local preparations like ointment, gel, powder or as lotions. As preparation for inhalation, sprays can be used.

The natural dialysis concentrate from deproteinized blood can be employed at the dose levels for example between 1–40 mg/kg, preferably 2–20 mg/kg. In experimental studies on the mouse surprisingly it was found that the formulation of invention shows excellent retinotropic effects. The following experimental set up was employed:

Mice were dark adapted for 12 hours and were then treated with the combination formulation as described in this invention. Thirty minutes later the damaging dose of the allylalkohol, 100 mg/kg was given intraperitoneally. After 27 min. the animals were anesthetized with 2500 mg/kg urethane, connected to the ERG apparatus and 3 minutes later the ERG was recorded. The results described in the following table relate to the b-wave potentials of the ERG.

| Results: | | |
|---|---|---|
| reference | treatment | Protection in % of the damage |
| damaging agent | Allylalkohol | — |
| 1. comparison | Calciumdobesilate 25 mg/kg | 0 |
| 2. comparison | bloodextract = 4 mg/kg | 0 |
| 3. comparison | 1-methyl-5-ethyl-7-(5-n- | |

-continued

Results:

| reference | treatment | Protection in % of the damage |
|---|---|---|
| | oxohexyl)-pyrazolopyrimidine 1 mg/kg | 15 |
| 4. comparison | pyridonyl-1-(n-hexanon-5), 25 mg/kg | 10 |
| 5. invention | calciumdobesilate (25 mg/kg) + bloodextract 4 mg/kg | 56 |
| 6. comparison | pentoxyfyllin 25 mg/kg | 0 |
| 7. invention | pentoxyfylline 25 mg/kg + bloodextract 4 mg/kg | 55 |
| 8. invention | 1-methyl-5-ethyl-7-(5-n-oxohexyl)-pyrazolopyrimidine 1 mg/kg + 4 mg/kg blood extract | 50 |
| 9. invention | pyridonyl-1-(n-hexanon-5), 25 mg/kg + bloodextract 4 mg/kg | 40 |
| 10. invention | Ca—dobesilate 12,5 mg/kg pentoxifyllin 12,5 mg/kg bloodextract 4 mg/kg | 65 |

1-methyl-5-ethyl-7-(5n-oxohexal)-pyrazolopyrimidine has the following structure:

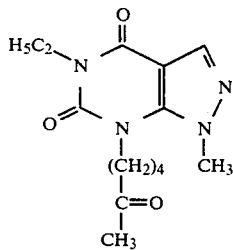

and
Pyridonyl-1-(n-hexanon-5) the following formula:

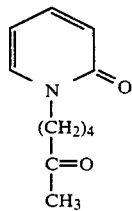

The foregoing table shows that at threshold dose levels the individual components do not exhibit protection towards allylalkohol damage.

The combination at the same dose levels unexpectedly however, is highly effective in antagonizing the alkohol injury to ERG b-wave function.

As seen from the last three lines of the table, compareable effect by the individual vasoactive compounds is produced at four times higher dose level and at 10 times higher dosage of the bloodextract.

The results shown in the table have been achieved in a double blind study. The animals obtained a constant volume of the samples of 0.1 ml/10 g mice. Besides the synergistic effect of the compositions the toxicity of the vasoactive compounds is considerably reduced. For example the $DL_{50}$ (i.p. mouse) for pentoxifyllin is 239 mg/kg, at 300 mg/kg it produces 100% mortality.

In combination with the blood extract according to the invention (about 400 mg/kg mouse) this mortality is completely abolished.

Keeping in view the long term treatment with the vasoactive drugs, which may extend to several years, the diminshing of the toxicity in combination with the blood extract, the invention has to considered as a remarkable advancement in the therapy of human beings with vasoactive drugs.

EXAMPLES

Equal amounts of calciumdobesilate and pentoxifyllin were dissolved in aqueous solution of the 0.04% to 0.4% of the blood extract. A single dose contains 60 to 100 mg dobesilate, 25 to 100 mg pentoxifyllin and 1 to 10 mg of the blood extract.

A formulation of similar composition can be prepared by combining similar amounts of the solid ingredients with usual pharmaceutically compatible carriers. Analog formulations can be manufactured from blood extract in combination with the other vasoactive components described in the invention i.e. the vincamine, nicergoline and the pyrazolopyrimidines or the pyridones. For the preparation of therapeutic formulations $\frac{1}{4}$ to 1/10 of the usual doses is employed in combination with the blood extract.

EXAMPLE 2

Solution for injection:
 Pentoxifyllin: 40 mg
 blood extract: 20 mg
 isotonic NaCl-solution ad: 5 ml

EXAMPLE 3

Solution for infusion:
 Vincamine: 800 mg
 blood extract: 3000 mg
 10% glucose solution ad: 1 l

EXAMPLE 4

1000 tablets:
 Pentifyllin: 100 g
 blood extract: 20 g
 carrier: 80 g

Examples for the synthesis of pyrazolopyrimidines of the formula II 1. 5-n-hexyl-4,5,6,7-tetrahydro-7-methyl-4,6-dioxo-1H-pyrazolo-[3,4-d]-pyrimidin Into a mixture of 3 g of $POCl_3$ and 10 of dimethylformamide 3 g of the 1-hexyl-3-methyl-4-hydrazinouracil are added under constant stirring, while cooling in an ice bath. The reaction mixture is allowed to come to the room temperature and stirred for further 30 min.. This is then poured onto ice. The reaction product separates out. Similarly the 1-N substituted product is obtained while the α-N-methylhydrazinouracil with the other substituents at the heterocyclic ring N-atoms is employed.

2. 2-ethyl-5-n-hexyl-4,5,6,7-tetrahydro-7-methyl-4,6-dioxo-2H-pyrazolo-[3,4-d]-pyrimidine 2,5 g of the product of example 1 is suspended in 20 ml of acetone and to it is added 10 ml of the ethylbromide. After addition of 3 g of $K_2CO_3$ the mixture was refluxed for 20 hrs. Filtration and evaporation of liquid phase yielded almost in quantitative yield the title compound which could be recrystallized from ethanol-water. The product shows mp of 107° to 108° C.

In an analog manner the in 2-position substituted compounds cab be synthesized.

3. 7-hexyl-4,5,6,7-tetrahydro-1,5-dimethyl-4,6-dioxo-1H-pyrazolo-[3,4-d]-pyrimidin 9 g of 3-hexyl-1-methyl-4-α-N-methylhydrazinouracil are slowly added to a mixture of 9 g of POCl$_3$ abd 32 ml of dimethylformamide, while the reaction temperature is maintained at about 50° C. After 20 min. of standing at the room temperature the mixture becomes solid. Ice water is added under stirring and the separated crystals are filtered off. After a single recrystallization 9,5 g of pure product is obtained. The mp is 106°–107° C.

4. 7-ethyl-4,5,6,7-tetrahydro-1-methyl-4,6-dioxo-5-(5-oxo-n-hexyl)-1H-pyrazolo-[3,4-d]pyrimidine 23 g of sodium salt of 7-ethyl-4,5,6,7-tetrahydro-1-methyl-4,6-dioxo-1H-pyrazolo-[3,4-d]-pyrimidine is dissolved in 150 ml of water at 50° C. At reflux temperature 1-chlorohexanon-5 is added slowly while stirring. The mixture is refluxed for 3 hrs. After distillation in vacuo the residue is dissolved in 250 ml of chloroform and extracted twice with each 2% solution of NaOH. The organic phase is washed with water and dried over sodium-sulfate. Removal of the chloroform leaves 19 g of the title compound of the mp 111.5° C.

I claim:

1. A composition for increasing oxygen supply in tissue of warm-blooded animals comprising at least one vasoactive compound selected from the group consisting of (a) calcium 2,5-dihydroxy-phenylsulfonate, (b) 3,7-dihydro-3,7-dialkyl-1H-purine-2,6-dione of the formulae

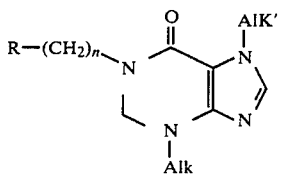

wherein AlK and AlK' are individually alkyl of 1 to 4 carbon atoms, n is an integer from 2 to 4 and R is selected from the group consisting of

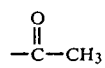

and —CH$_2$—CH$_3$, (c) a pyrazolo-[3,4-d]pyrimidines of the formulae

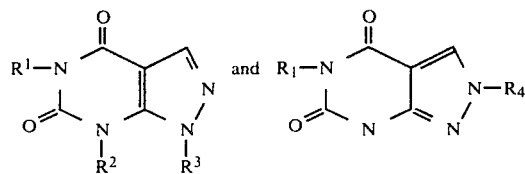

wherein R$^1$ and R$^2$ are individually selected from the group consisting of hydrogen, alkyl of 1 to 8 carbon atoms, alkenyl of 2 to 8 carbon atoms and alkylcarbonylalkyl of 4 to 8 carbon atoms, R$^3$ is selected from the group consisting of hydrogen and alkyl of 1 to 4 carbon atoms and R$^4$ is selected from the group consisting of hydrogen, alkyl of 1 to 6 carbon atoms and alkenyl of 2 to 6 carbon atoms with the proviso that R$^1$ and R$^2$ are not both hydrogens, (d) a pyridone of the formula

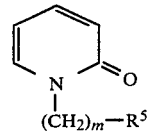

wherein m is an integer from 2 to 4 and R$^5$ is selected from the group consisting of

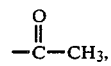

—CH$_2$—CH$_3$ and —CH$_2$—CH$_2$—OH and (e) a compound selected from the group consisting of nicergoline, vincamine and dipyridamol and a potentiating amount of a lipid-free dialyzed concentrate of deproteinized, enzymatically hydrolyzed calf's blood with the blood constituents having a molecular weight less than 10,000.

2. A composition of claim 1 wherein the vasocative compound is a pyrazolo-[3,4-d]-pyrimidine and R$^1$ and R$^3$ are methyl or ethyl and R$^2$ is

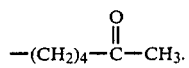

3. The composition of claim 1 wherein the vasocative compound is pentoxifyllin.

4. The composition of claim 1 wherein the vasocative compound is selected from the group consisting of calcium 2,5-dihydroxy-phenylsulfonate, 1-methyl-5-ethyl-7-(5-n-oxohexyl)pyrazolopyrimidine and pyridonyl-1-(n-hexanon-5).

5. A method of increasing the oxygen supply in the tissue of warm-blooded animals comprising administering to warm-blooded animals a sufficient amount of a composition of claim 1 to increase the oxygen supply in the tissue.

6. A method of claim 5 wherein the vasocative compound is a pyrazolo-[3,4-d]-pyrimidine and R$^1$ and R$^3$ are methyl or ethyl and R$^2$ is

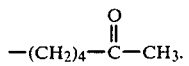

7. A method of claim 5 wherein the vasocative compound is pentoxifyllin.

8. A method of claim 5 wherein the vasocative compound is selected from the group consisting of calcium 2,5-dihydroxyphenylsulfonate, 1-methyl-5-ethyl-7-(5-n-oxohexyl)-pyrazolopyrimidine and pyridonyl-1-(n-hexanon-5).

* * * * *